United States Patent [19]
Dwight

[11] 4,355,980
[45] Oct. 26, 1982

[54] METHOD OF FORMING DENTAL RESTORATIONS

[76] Inventor: Owen Dwight, 440 Calle Madrigal, Cathedral City, Calif. 92234

[21] Appl. No.: 207,410
[22] Filed: Nov. 17, 1980
[51] Int. Cl.³ .............................................. A61C 5/04
[52] U.S. Cl. .................................... 433/226; 433/228
[58] Field of Search ............... 433/228, 222, 218, 206, 433/207, 208, 200, 214, 215, 223, 226; 264/19, 16; 164/DIG. 4

[56] References Cited

U.S. PATENT DOCUMENTS

| | | | |
|---|---|---|---|
| 833,883 | 10/1906 | Lentz | 164/DIG. 4 |
| 1,013,666 | 1/1912 | Lederle | 164/DIG. 4 |
| 1,090,939 | 3/1914 | Newton | 164/DIG. 4 |
| 1,209,906 | 12/1916 | Thurston | 433/226 |
| 1,379,063 | 5/1921 | Van Allen | 433/218 |
| 1,457,370 | 6/1923 | Jefferies | 164/DIG. 4 |
| 1,465,472 | 8/1923 | Hansen | 433/223 |
| 2,206,502 | 7/1940 | Heiligman | 433/228 |
| 3,834,024 | 9/1974 | Kochari | 433/207 |
| 3,997,637 | 12/1976 | Rogers | 264/19 |
| 4,064,629 | 12/1977 | Stoner et al. | 433/226 |

FOREIGN PATENT DOCUMENTS

| | | | |
|---|---|---|---|
| 54-132426 | 10/1979 | Japan | 433/228 |
| 7700678 | 1/1976 | Netherlands | 433/228 |

Primary Examiner—Gene Mancene
Assistant Examiner—John J. Wilson
Attorney, Agent, or Firm—I. Louis Wolk

[57] ABSTRACT

This invention relates to a novel method for preparing dental restorations and the product, thereof, in which a relatively hard alloy is utilized for casting a crown or inlay and a softer, more malleable alloy in particulate form is positioned in the mold prior to the casting operation in the marginal areas of the restoration to provide better adaptation to the gingival margins and/or to the tooth structure.

3 Claims, 15 Drawing Figures

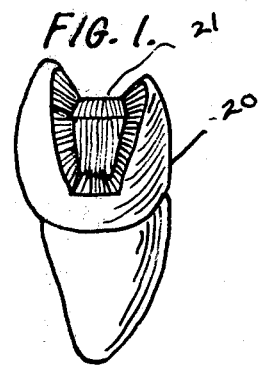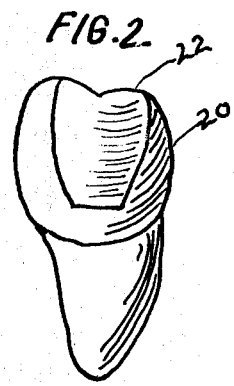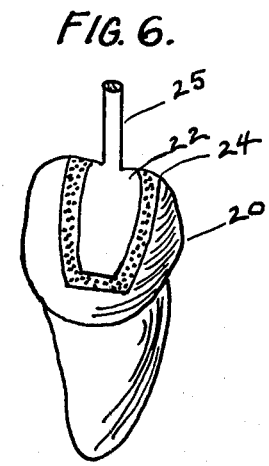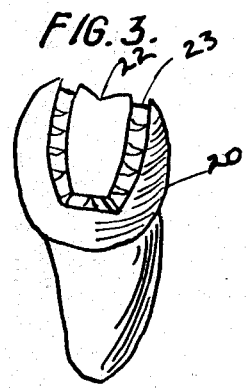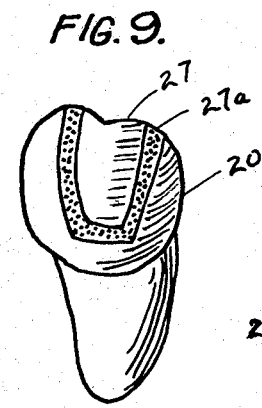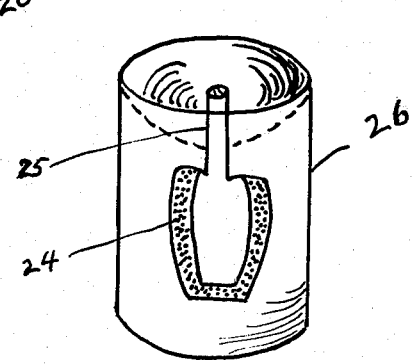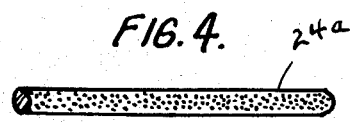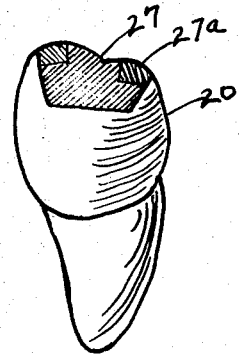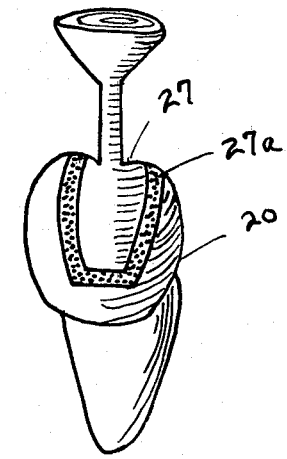

METHOD OF FORMING DENTAL RESTORATIONS

BACKGROUND OF THE INVENTION

This invention relates to a novel method for the production of dental restorations and products produced thereby which permits the advantageous and economical use of gold in combination with other conventional alloys such as silver-palladium, low gold contact alloys and the like. The greatly increased cost of gold as a preferred material for making dental restorations such as crowns, inlays and bridgework has stimulated a greater degree of interest in the use of other less costly materials such as the alloys referred to. However, such alloys have certain disadvantages since they do not permit suitable marginal adoption to the gums, in the case of crowns, or to the interiors of cavities, in the case of inlays.

Casting gold alloys are classified by the American Dental Association according to their hardness, as determined by their resistance to indentation, into four groups: soft, medium, hard and extra hard, Types I, II, III, and IV respectively. Type I, for example, has a gold content of about 80-90%, Type II, 73-83%, Type III, 71-80% Type IV, 62-72%. Silver, copper, palladium and zinc are present in varying proportions.

Dental casting alloys containing relatively low proportions of gold have been available for many years but are now attracting a high degree of interest due to the great increase in the price of gold. In general, these alloys are harder and more durable than high gold content alloys. A review of low gold content alloys is contained in a report by the American Dental Association in JADA Vol. 100, February 1980, Pages 237-240. Palladium - silver based alloys containing little or no gold, have been developed as substitutes for higher gold content alloys as reported in JADA Vol. 89, August 1874, Pages 383-385 and in literature and patents referred to therein. Such alloys, as well as the low and medium gold alloys referred to above, are highly suitable for use as the primary component of the restorations to be used with the present invention. A serious problem inherent with the use of lower gold content alloys, or such alloys as palladium-silver referred to, is the fact that their hardness precludes close marginal adaptation to the tooth structure and exposes more cement at the seal margins. Throughout the history of dentistry, gold or high gold alloys have been the metals of choice for crowns or inlays because of their marginal adaptivity, since the life of an inlay or crown depends upon good marginal adaptation and smaller cement exposure.

SUMMARY OF THE INVENTION

Applicant has now discovered and developed a novel composite casting process which joins together in one operation within the casting mold itself, two metals or alloys which permit the use of low or no gold content alloys as the major component of the restoration while providing a pure or higher gold content region located at the marginal area of the product to permit suitable adaptation to the tooth structure. This is accomplished by forming grooves or marginal cut out areas in the wax pattern of the inlay or crown and incorporating in said grooves a comoposition composed essentially of particles of gold or a gold alloy bound together with a small proportion of a binder to hold the particles together to permit manipulation by the dentist to comform to the desired dimensions of the pattern and fill in the cutout marginal areas. This composition of gold or high gold alloy particles preferably has a gold particle content of 95% or more with the rest being a binder such as a dental wax or other similar material such as petroleum wax or a gum such as agar, gum arabic or similar natural or artifical gums or resins which will have suitable binding properties while still allowing the particle composition to be plastic enough to be worked in order to fill the grooves referred to.

The gold alloy particles referred to may be of any desired gold content as long as they form a film which is sufficiently malleable to be adapted to the margins of the tooth and are softer than the alloy of the casting alloys having a gold content higher than 50% have been found to be highly suitable.

In essence, applicant has invented a process which enables the preparation of a restoration of the type described herein, in which the major component, which is subject to the greatest stress and wear, is formed of a relatively hard and durable precious metal alloy with a low gold content or one with no gold content and in which the marginal areas which require adaptation to the tooth structure and which represent only a small portion of the total volume, are composed of a softer alloy of higher gold content to permit adaptation to the tooth or gums and permits formation of a close marginal seal with minimal cement exposure. Since the softer margins are relatively thin and are blended with and supported by the harder alloy forming the bulk of the restoration, they are strongly supported by the harder base alloy in addition to being sufficiently malleable to permit proper adaptation.

One such composition is preferably formed of finely divided gold powder or filings dispersed in wax, shaped in the form of a small diameter rod or narrow strip. Another such composition may be formed by mixing the gold or gold alloy particles with a dental utility wax with just enough wax to make the mixture plastic to form a heavy paste.

In general terms the novel procedure referred to is utilized in connection with conventional practice in the preparation of restorations. In so doing, an impression is prepared from the patient's mouth. At the laboratory a "stone" or plaster cast is prepared and a working model of the tooth is produced. The male casting, which represents the patient's tooth, after preparation to define the cavity or contour to which the inlay or crown is to be supplied, is called the "die". In conventional practice, a wax inlay pattern or wax crown is formed on the "die", a wax sprue is attached and the wax patterern is positioned in a casting ring. An investment material is then used to fill the casting ring and after it sets, is heated to remove the wax. The investment casting then has cavity corresponding to the removed wax and sprue and is then positioned in association with a centrifugal casting machine. A pellet of gold or alloy which is to be used in the restoration is melted and cast into the investment cavity by centrifugal force.

In carrying out the present invention, grooves or marginal cut-out areas are formed in the wax inlay pattern, preferably 1 to 1.5 mm in width and depth, or in the case of a crown, gingival margins are cut out to a similar width and depth and the composite formulation containing particulate gold or gold alloy dispersed therein is used to fill in the cut out areas. In one convenient procedure, the gold-wax composition is first formed into rods having a diameter conforming to the dimensions of the cut out margins and such rods are inserted or laid into said margins, as more fully described below. The wax-gold composition is formed of a wax such as a soft dental utility wax also known as boxing or carding wax into which 95 to 98% by volume of dust or filings or similar particles of gold or a high gold alloy having a particular size ranging from that of dust of a few microns to larger particles up to say 0.25 millemeters in diameter. A preferred particle size has been found to be about 0.01 millemeters. This is done by softening or melting the wax, then adding the gold particles while stirring to disperse the gold and at the same time, allowing the wax to harden. To form the rods, the composition may be extruded to the proper diameter and convenient length for handling. Instead of rods, the wax-gold composition may be formed into strips of rectangular or oval cross sections. These rods may then be packaged in lengths ranging from 2–6 inches.

As an alernative to the use of particle composition in the form of rods, the gold or gold alloy particles, after mixing with the wax, or other selected binder, is formed into a heavy paste and the paste material is applied to the grooves in the inlay or crown patterns by means of small spatula and shaped to conform to the final shape of the pattern. This material may be packaged in jars or collapsible tubes.

In practice, the gold particle composition, if in the form of a rod or cylinder, is pressed into the cut-out groove with finger pressure and then pressed more firmly into the groove with a flat blade wax insturment. If a paste formulation is used, it can be applied to the groove with a suitable tool. After the particle composition is in place, it is luted to the body of the wax pattern with the tool and if the wax binder is used, the tool may be heated. In any case, the contour of the pattern is carefully restored in the filling in the cut out area. The resulting composite wax pattern carrying the wax-gold composition has a sprue applied and is removed from the "die" and invested into a ring for casting in the conventional manner. When the wax is removed from the casting mold ring, prior to the final casting with the desired alloy, the gold or gold alloy from the wax marginal insert is deposited along the desired marginal areas and retains its form and position within or upon the final "die", and during the alloy casting operation, is melted and either is uniformaly bonded in a thin film along the marginal areas of the cast alloy or is surface alloyed depending on the composition of the casting material. In either case, the critical marginal area is of gold or of substantial gold content so that it may be readily adapted to the tooth surface and/or the gingival areas as the case may be. The sprue referred to above may be of wax or of plastic as in conventional practice.

BRIEF DESCRIPTION OF THE DRAWINGS

In the drawings:

FIG. 1 is a view in perspective of a stone die conforming to a tooth having a prepared cavity.

FIG. 2 is a view similar to FIG. 1 in which a wax inlay pattern has been formed.

FIG. 3 is a view showing the wax pattern of FIG. 2 with wax margins cut out.

FIG. 4 is a view of a wax rod having gold particles dispersed therein.

FIG. 5 is a view showing the cut-out margins of FIG. 3 with the rod of FIG. 4 in place.

FIG. 6 is a view in perspective showing a wax sprue attached to the wax pattern.

FIG. 7 is a view showing the wax pattern and sprue assembly of FIG. 6 positioned in an investing ring.

FIG. 8 is a view showing the inlay with sprue attached to preparatory final polishing.

FIG. 9 is a view in perspective of a completed inlay in a tooth.

FIG. 10 is a view in partial vertical cross section of the inlay of FIG. 9.

DESCRIPTION OF THE PREFERRED EMBODIMENTS

Figure 12:
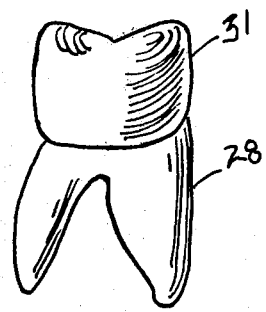
FIG. 12 is a view showing the die of FIG. 11 provided with a wax crown conforming to the desired molar configuration.

Referring to the drawings in detail, as shown in FIG. 1, a stone die 20 is prepared from the impression of the tooth as described above, in the case of a cavity to be corrected by means of an inlay, the cavity after preparation by the dentist is shown at 21. In FIG. 2, inlay wax 22 is applied to the cavity in the proper manner. In FIG. 3, the margins of the wax outlining the cavity are cut out or recessed by a hand tool or a small burred outlining tool operated by an electric hand drill to form a continuous groove 23 to accommodate the insertion of a strip or rod of the wax-gold particle composition 24a illustrated in FIG. 4. The dimensions of the groove, and of the wax-gold composition may vary but preferably are about 1 to 1.5 mm. in width and depth. The wax-gold composition is pressed into the groove and the surface smoothed out to properly conform to the die as shown in FIG. 5. A sprue 25 is then attached to wax 24 in conventional manner as shown in FIG. 6. The wax inlay pattern, with the wax-gold marginal insert and the attached sprue, are then removed from the die and positioned within an investment casting ring 26 as shown in FIG. 7. The ring is then filled with investment material surrounding the pattern and after setting of the material, it is heated and the wax melted or burnt at a suitable temperature, say 1200° F., leaving a cavity corresponding to the cavity to be replaced with the inlay. At the same time, the gold particles contained in the marginal wax-gold insert remain in position in the cavity.

The mold is now ready for casting and this is carried out in conventional manner as by centrifugal casting of a molten pellet of the alloy to be used. One suitable alloy is a conventional silver-palladium alloy known to the dental professional as "Alborium", containing 15% Av, 25% Pd and 45% Ag, the casting temperature of which is 2050°–2150° F. The mold itself, remains heated for example at about 1000° F. while the casting alloy is introduced in its molten state.

After casting and cooling of the mold, the inlay 27 with a metal sprue 25 attached, is mounted on the die for removal of the sprue and final polishing as shown in FIG. 8. As shown, the casting is composed of the alloy 27 with the marginal areas which would be in contact with the surface of the tooth composed of gold or gold alloy 27a bonded to and/or alloyed with the material of the alloy. When the inlay is installed in the tooth cavity, the higher gold content margins are adaptable and can be fitted and polished to provide the necessary smooth and tightly sealed surface.

FIGS. 9 and 10 illustrate the inlay 27 with marginal softer alloy 27a shown as a distinct region but in fact, the marginal segment is intimately bonded to and alloyed with the alloy of the inlay 27.

Figure 11:
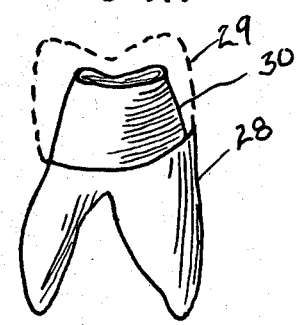
FIG. 11 is a view in perspective of a die conforming to a molar, with preparation for a crown.
Figure 13:
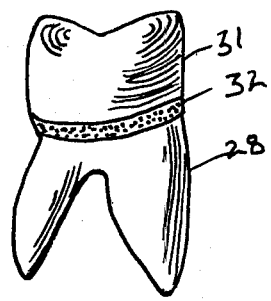
FIG. 13 is a view in perspective showing the wax-gold composition incorporated along the gingival area.
Figure 14:
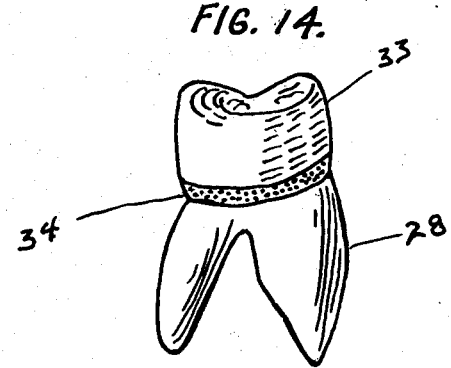
FIG. 14 shows a finished molar alloy crown in place on a tooth with soft adaptable gold margins.
Figure 15:
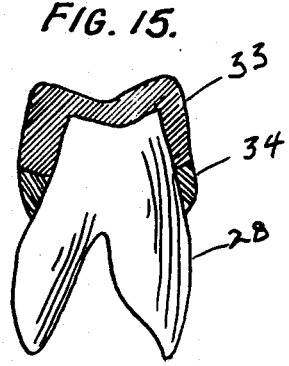
FIG. 15 is a view showing the crown of FIG. 14 in vertical cross section.

FIGS. 11, 12, 13, 14 and 15 illustrate the invention as applied to a molar crown. In FIG. 11, stone die 28 is shown with area 29 shown in the dotted lines conforming to the surface of the tooth prior to preparation and 30 showing the prepared surface. In FIG. 12, wax crown 31 is applied to the die and FIG. 13 shows the wax crown 31 with the marginal or gingival area shown with the gold-wax composition 32 inserted after cutting out a groove having the necessary dimensions, which as discussed with respect to the inlay, are preferably 1–1.5 mm. wide and deep FIG. 14 shows the finished Crown 33 with the marginal soft alloy area 34 while FIG. 15 shows the crown 33 with the soft marginal portion 34 in vertical cross section. Although the marginal area is shown with a line of demarcation, this is for purposes of illustration, since in practice, the soft and hard components are alloyed together at the junction and a sharp demarcation does not occur.

After investment, removal of the wax, and casting with the desired alloy, i.e. silver-palladium, the finished crown is cemented to the tooth in conventional manner. The gingival margins being composed of higher gold content alloyed to the silver-palladium permits proper adaptation to the tooth and gum.

I claim:

1. A method of forming dental restorations which comprises incorporating within a mold cavity conforming to the shape of the desired restoration finely divided particles of gold or relatively soft gold alloy only along an area corresponding to the exposed marginal area of the restoration contiguous to the tooth or gum, and thereafter casting within said cavity a relatively harder dental alloy, said particles and said harder alloy becoming bonded together to form a composite structure in which softer marginal areas are formed to permit improved adaptation of the restoration to the tooth and/or gum.

2. A method according to claim 1 wherein the relatively hard alloy is an alloy selected from the class consisting of alloys comprising gold, metals of the platinum group, silver, and mixtures thereof, and the softer alloy comprises gold or an alloy thereof.

3. A method of forming dental restorations which comprises forming a wax pattern corresponding to the restoration to be applied to a tooth, forming a groove around edges of the pattern along the margins thereof, filling said groove with particles of gold or gold alloy, surrounding the resulting wax pattern with investment material, heating to remove the wax and thereby forming a mold cavity with gold particles deposited therein along areas corresponding to the margins of the desired restoration, and casting within said cavity a dental alloy of desired hardness and at the same time melting said gold particles whereby said alloy becomes bonded to said gold to form a soft gold containing marginal area.

* * * * *